United States Patent [19]

Rosenberg

[11] Patent Number: 4,571,178
[45] Date of Patent: Feb. 18, 1986

[54] FORWARD-BACKWARD MOLAR CONTROLLING AND POSITIONING DENTAL APPLIANCE

[76] Inventor: Farel A. Rosenberg, 10535 Wilshire Blvd., #1811, Los Angeles, Calif. 90024

[21] Appl. No.: 679,472

[22] Filed: Dec. 7, 1984

[51] Int. Cl.⁴ ............................................. A61C 3/00
[52] U.S. Cl. ...................................... 433/18; 433/7; 433/19
[58] Field of Search .................... 433/18, 21, 23, 24, 433/7, 6, 19

[56] References Cited

U.S. PATENT DOCUMENTS

| | | | |
|---|---|---|---|
| 1,582,570 | 4/1926 | Brust | 433/7 |
| 1,908,853 | 5/1933 | Linde | 433/7 |
| 3,293,747 | 12/1966 | Denholtz | 433/21 |
| 3,800,420 | 4/1974 | Ouaknine | 433/7 |
| 3,835,540 | 9/1974 | Biederman | 433/7 |
| 4,431,411 | 2/1984 | Witzig et al. | 433/6 |
| 4,468,196 | 8/1984 | Keller | 433/24 |

FOREIGN PATENT DOCUMENTS

| | | | |
|---|---|---|---|
| 1110363 | 7/1961 | Fed. Rep. of Germany | 433/19 |
| 483374 | 4/1938 | United Kingdom | 433/7 |

*Primary Examiner*—John J. Wilson
*Attorney, Agent, or Firm*—Gilbert Kivenson

[57] ABSTRACT

This invention relates to a dental appliance which can be used to produce backward molar movement when desirable in orthodontic treatment, to control forward movement of molars and adjacent teeth and to stabilize molars and adjacent teeth against forward movement when these teeth are being used as anchoring points.

5 Claims, 7 Drawing Figures

FORWARD-BACKWARD MOLAR CONTROLLING AND POSITIONING DENTAL APPLIANCE

BACKGROUND OF THE INVENTION

It is often the case in orthodontic practice that crowdings in the upper and lower dental arch or other orthodontic problems such as protrusion are overcome by extracting first or second bicuspids or molars to create space and then moving the surrounding teeth into that remaining space. Controlled tooth movement is brought about by first cementing orthodontic bands with welded-on hooks around the teeth to be moved and similar bands on the first molars or other teeth acting as anchors. Tooth moving forces are, in present practice, created by attaching springs or elastic cords between the hooks (on the cheek side) in front of and behind the extraction site. One problem with this technique is that reactive forces will cause unwanted movement of the molar or other anchor teeth and the loss of control of the process. The reactive force on the first molars may be reduced, but not controlled, by banding and linking them to the second molars behind them. The present invention controls the above mentioned forward molar movement without the need for additional banding.

A major use of the invention can be found when second molars are extracted in preference to the more visable first and second premolars bicuspids and then moving the first molars and other forwardly positioned teeth backward into the created spaces as dictated by the particular dental needs of the patient. Molars are difficult to move in a backward direction. Solutions to the problem of finding suitable backward molar forces have involved external harnesses which use the neck or cranium (cervical straps, head gear or combinations of these). Although the backward molar forces thus obtained are adequate, the arrangement is bulky, unsightly and uncomfortable. Patient cooperation is therefore difficult to obtain. As an alternative to the external apparatus mentioned above, backward forces have been obtained by utilizing the unyielding, tissue-covered basal bone in particular areas just behind the upper and lower front teeth (in the area of the root tips). This can be done through an upper (maxilliary) palatal pad resting on the highest, most frontal portion of the palatal vault above the roots of the front teeth or a similar pair of pads resting on either side of the frenum of the tongue in the area of the root tips of the lower front teeth.

Perhaps the best known of these appliances is the "Nance Holding Arch". In this passive device a palatal pad molded of acrylic plastic is used. Imbedded in the plastic are heavy wires which extend to and are soldered to orthodontic bands. The latter are then cemented to back teeth such as the upper first or second molars. During the necessary laboratory assembly of the holding arch, the wires are joined to the tongue side of the orthodontic bands and are made of such length as to allow the pad to rest on the palate when the appliance is installed. The Nance device has no mechanisms to move molars backwardly or to control their forward movement.

Another removable anchoring appliance was invented by Bedell for the lower teeth. This anchorage is held in place by wire clasps connecting it temporarily to various teeth and by vertical posts inserted into vertical tubes on the tongue side of affixed orthodontic bands. It is necessary to custom fabricate the Bedell appliance in a laboratory for each patient. It is a removable appliance (by the patient) and thus requires his full cooperation.

An additional appliance used for anchoring in the upper or lower dental arch is the "lip bumper". In its simplest form the lip bumper consists of a padded, horse-shoe shaped wire installed with its pad resting between the lip and the front teeth but separated from the latter and maintained at a given distance during usage to produce limited backward pressure on the posterior teeth. With the ends of the wire inserted into tubes on the cheek side of orthodontic bands on first or second molars, lip pressure is transferred to backward molar movement by preventing the wires from freely sliding through their respective molar tubes through the use of mechanical stops. The device produces limited dental movement, is uncomfortable, produces an unsightly protrusion of the lower or upper lip and may cause unwanted forward movement of the incisors.

DESCRIPTION OF THE DRAWINGS AND THE OBJECTIVES OF THE INVENTION

The operation of the invention will be described with references to FIGS. 1, 2, 3, 4, 5, 6 and 7.

FIGS. 1 and 2 illustrate a condition of misalignment (crowding) often found in children. In FIG. 1, a top view of the lower teeth, a bicuspid on each side has been extracted to create space for correcting the overcrowding problem.

In FIG. 2, a top view of the upper teeth, second molars have been extracted on each side for the same purpose, creating space.

Figure 5:
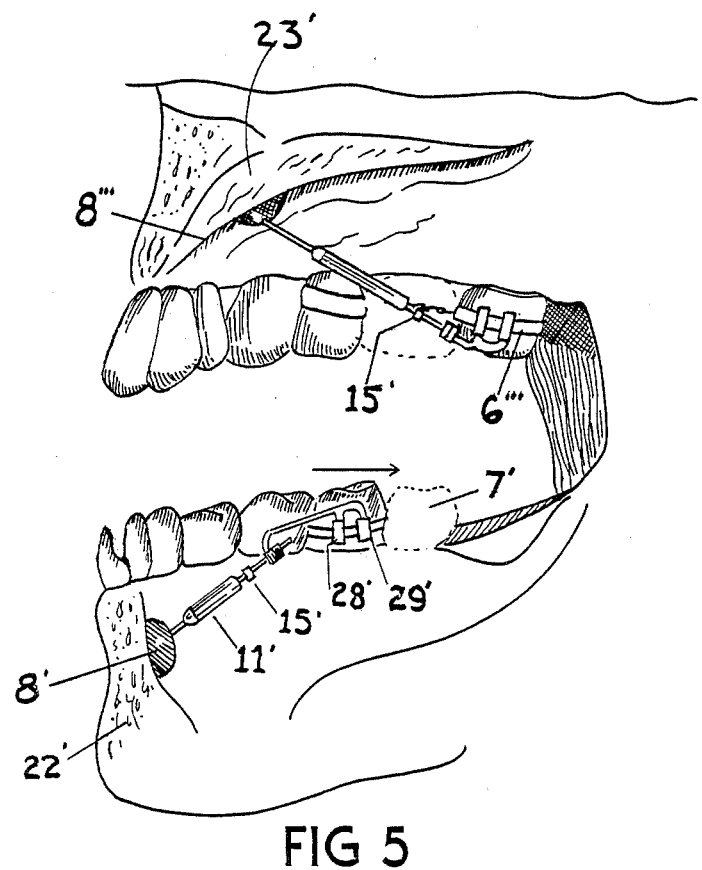

FIG. 5 is a sagittal view of the upper and lower teeth, their supporting skeletal structure and the basal bony areas. In the upper teeth of FIG. 5 the invention is being used in one of its modes, preventing or limiting forward movement of anchor teeth. In the lower teeth of the drawing the invention is being used in another of its modes, moving a molar rearwardly.

Figure 6:
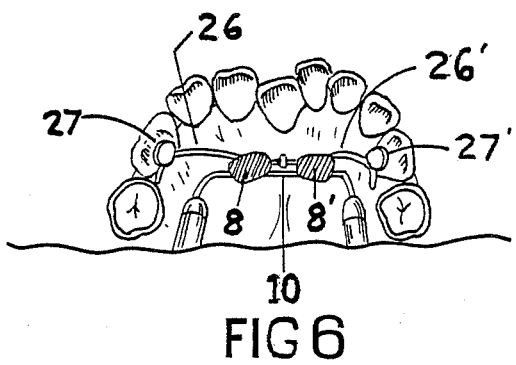

FIG. 6 is a top view of a second embodiment of the invention as used in the lower dental area. In this embodiment, stabilizing wires are used to aid in retention of the appliance.

Figure 7:
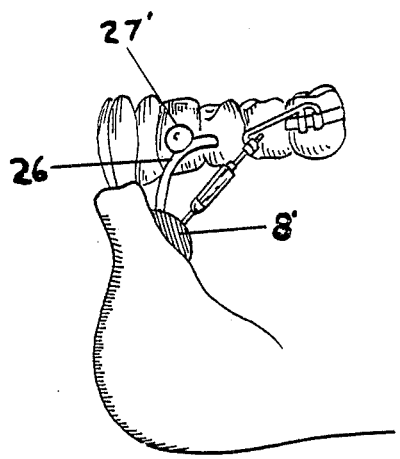

FIG. 7 is a sagittal view of the second embodiment in place in the lower teeth.

Figure 1:
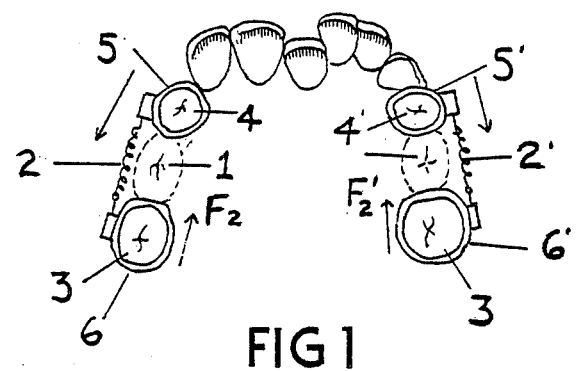

The condition shown in FIG. 1 is caused by overcrowding of the teeth. The front teeth are not in normal positions because the dental arch is too small to accommodate them. A common treatment for this condition is to initially extract a tooth in each side of the dental arch such as the first or second premolars (bicuspids) to create two spaces. The remaining teeth forward of these spaces are then moved backwardly to relieve the crowding. In FIG. 1 the second bicuspids 1 and 1' are shown removed. Bands 5, 5', 6 and 6' (provided with side bracket slots, tubes and hooks) are then cemented to the remaining bicuspids 4 and 4' and the molars 3 and 3' respectively. Springs or elastic cords 2 and 2' are stretched between the hooks on opposite sides of the extraction sites. Over a period of time the first bicuspids 4 and 4' (and later the teeth forward of them with separate but similar arrangements) will be moved backwards into the extraction spaces and thus produce overall normalization of the patient's tooth positions.

Unfortunately the corrective forces $F_1$ and $F_1'$ which bring about crowding correction and backward movement of the anterior teeth are accompanied by the reactive forces $F_2$ and $F_2'$. The latter tend to produce undesired and uncontrolled forward motion of the molars 3 and 3'. It is an objective of the present invention to prevent or control the forward movement of molar teeth used as anchors.

In some instances both backward movement of the anterior teeth and the bicuspids 4 and 4' and forward movement of the molars 3 and 3' into the extraction sites 1 and 1' are desired. Another objective of the invention therefore is to permit this forward molar motion in limited and controlled amounts and to bring it to a stop when desired.

Figure 2:
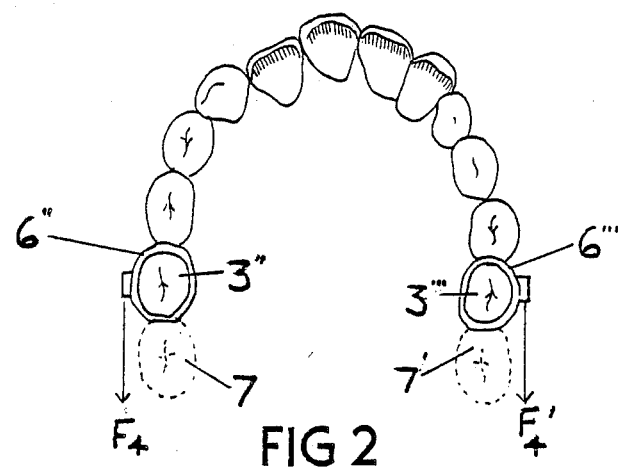

Another solution to the overcrowding problem is shown in FIG. 2. In this case the second molars 7 and 7' (of the upper teeth) have been extracted and the upper first molars 3 and 3' are to be moved, by means of external headgear, backwards into the extraction spaces. This makes room for the teeth forward of the molars to be moved backwardly and thus normalize their overall positioning. A still further objective of the present invention therefore is to make possible the exertion of continuous force necessary for the backward movement of the molars without the need for headgear and similar appliances requiring constant patient cooperation.

DESCRIPTION OF THE INVENTION

Figure 3:
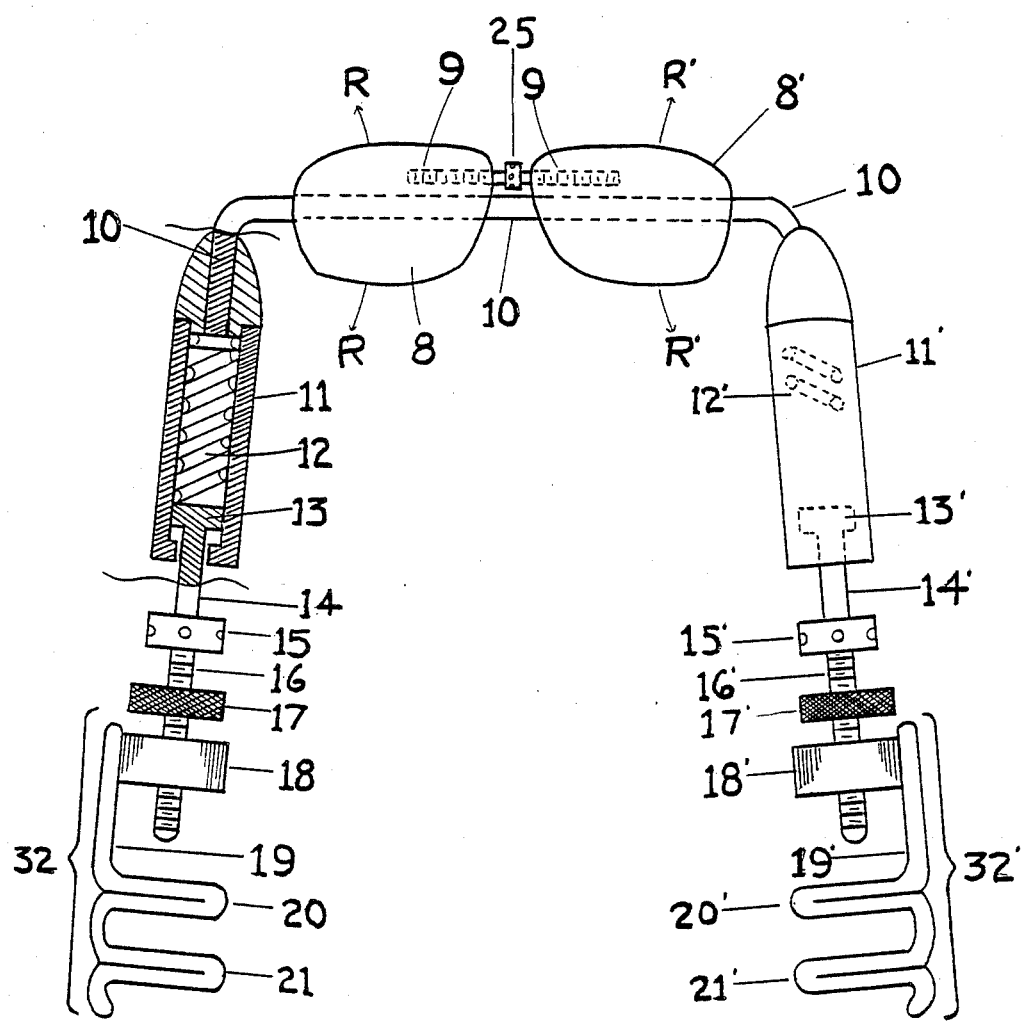
FIG. 3 is a top view of the invention prior to its installation in the mouth.

In the top view of the invention shown in FIG. 3 the padded plates 8 and 8' are joined by the right and left-handed threaded shaft 9 which is fitted into correspondingly prepared holes in the plates. The rod 10 passes through the plates and terminates at each end in the chambers 11 and 11'. The plates 8 and 8' are free to pivot on the rod 10 in the directions R and R' as shown. The enlarged knob 25, in conjunction with the oppositely threaded shaft 9, serves as a turning device for changing the distance between the padded plates as required for customized, stable seating in the patient's mouth. Although this construction bears some superficial resemblance to mid-palatal or suture stretching appliances such as those of Oakine (U.S. Pat. No. 3,800,420) or Biederman (U.S. Pat. No. 3,835,540), there is no relation between the objectives of the present invention and the intended uses of these appliances. The latter involve mid-palatal stretching or sutural splitting which the present invention does not attempt, nor can accomplish.

Figure 4:
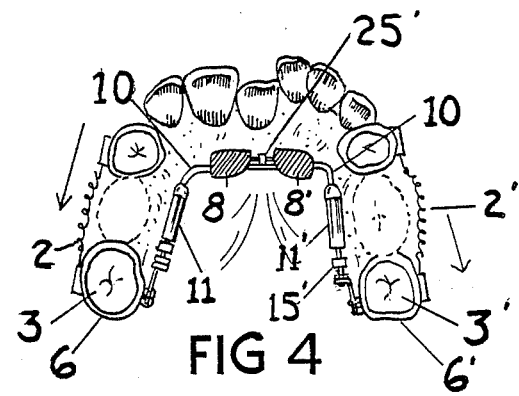
FIG. 4 shows how the invention would be installed for use in conjunction with the treatment of conditions shown in FIG. 1.

In the chambers 11 and 11' (FIG. 3) are the springs 12 and 12' and the piston heads 13 and 13'. The pistons connect to the threaded connecting lugs 18 and 18' by way of the piston rods 14 and 14', the adjustable turning devices 15 and 15', the threaded portions 16 and 16' of the piston rods and threaded holes in the corresponding connecting lugs 18 and 18'. The lock nuts 17 and 17' are tightened against the connecting lugs to secure the rotary position of the piston rods 14 and 14' as is known to the art. The connecting lugs 18 and 18' are welded to the attachment wires 19 and 19' which are formed into insertion loops 20, 20', 21 and 21'. The latter fit into tubes 28, 29, 28' and 29' in upper and lower dental arches. The tubes are attached to the tongue side of the bands 6 and 6' (FIGS. 4 and 5). It will now be apparent that the turning of knobs 15 and 15' will cause the pistons 13 and 13' to exert forces on the springs 12 and 12' and consequently on the forward portions of chambers 11 and 11', rods 10 and 10' and finally on the padded plates 8 and 8' (FIG. 3). The padded plates, by virture of their positions against tissue-covered, unyielding basal bone (22' and 23' in FIG. 5) will serve to prevent or limit forward motion of the molars.

The invention as used in conjunction with the corrective technique of extracting second molars is shown in the lower jaw portion of FIG. 5. In this case the entire force required for moving the first molar 3' backwards is exerted by the invention using the basal bone structure 22' as the force bearing foundation.

The appliance may be mounted in its holding tubes (28, 29, 28', and 29' FIG. 5) from the biting surface side as shown or from the gum side as the case needs require.

In some cases the oral cavity structure of a particular patient does not permit anchoring of the invention solely by the use of the padded plates 8 and 8' and the band attachments as previously described. A shallow upper or lower oral cavity with insufficient slope of the tissue covered surfaces may make it difficult to retain the invention in the mouth. In these cases the embodiment shown in FIGS. 6 and 7 will be useful. The stabilizing wires 26 and 26' are rigidly embedded in the padded plates 8 and 8'. During installation of the appliance the free ends of these wires are passed under the button fixtures 27 and 27' which can be attached to the tongue side surfaces of the appropriate teeth. The spring tension of the wires underneath the buttons produces a hold-in force which assures that the appliance will not move during chewing or as a result of varying tensioning adjustments made by the dentist. The stabilization wires are of such a length as to allow movement of the button-bearing teeth which contact them without disengagement.

Stabilization wires are also useful in retaining the appliance in the mouth when mounting has been from the gum side to help neutralize vertical force vectors.

The invention may also be applied as an adjunct to orthopedic (bone correcting) procedures in which molars are used as anchoring points. Certain other kinds of malocclusions between the upper and lower sets of teeth (such as are caused by underdeveloped lower jaws with their respective teeth abnormally behind the upper teeth) are corrected by linkages between the upper and lower sets of molars. These linkages move the lower jaw forward in a predetermined pattern with the result, over an interval of time, that the jaw is permanently advanced to a corrected forward position and a normal alignment between the upper and lower teeth is achieved. The present invention can in these cases be used to "brace" the lower molars being used to anchor the linkage and prevent their undesired forward movement. The plate portion of the padded plates 8 and 8' is preferably of a molded acrylic but can be of stainless steel or other hard material. The tissue-contacting, padded portion of the plates is custom applied by the dentist at the time of fitting of the appliance with a tissue-compatible, soft and resilient material such as silicone polymer. The latter then forms an integral part of these plates.

I claim:

1. A dental appliance for use in particular orthodontic procedures as a tooth movement inhibitor, inducer and controller comprised in combination of:

a. a pair of separated, padded plates shaped to bear against tissue covered, relatively unyielding basal bony areas and rotatably mounted about a primary rod which is terminated at either end by an adjustable force exerting member;
b. width adjusting means between said padded plates to be used to custom fit the appliance to either dental arch;
c. means for coupling said adjustable force exerting members to a pair of teeth selected for anchoring purposes at opposite, posterior ends of the dental arch;

whereby the anchorage provided between the teeth selected for anchoring purposes and the tissue covered basal bony areas is facilitated and improved by the rotatable feature of the padded plates which permits optimum contact.

2. A dental appliance as described in claim 1 in which the mounting of the padded plates permits them to rotate and assume positions of maximum immobility against the tissue covered bony areas as the adjustable forces are altered to achieve various amounts of tooth movement.

3. A dental appliance as described in claim 1 in which said adjustable force exerting members are partly comprised of the first rod which passes through the padded plates and terminates at each end against a spring coil contained in a hollow cylindrical chamber in each side of the mouth.

4. A dental appliance as described in claim 3 in which said spring coil in each hollow cylindrical chamber can be compressed by a piston head in contact with the other end of the spring coil, the piston head being attached to a piston rod which incorporates a knob with radial holes to facilitate pressure adjustment by turning and is threaded along a portion of its free end.

5. A dental appliance as described in claim 4 in which the threaded end of each of said piston rods is engaged in a threaded hole in a connecting lug secured by attachment loops to an anchor tooth, whereby turning of the piston alters the spring coil compression and controls the force generated between the basal bone and the corresponding anchor tooth.

* * * * *